(12) United States Patent
Sigler et al.

(10) Patent No.: US 7,642,059 B2
(45) Date of Patent: Jan. 5, 2010

(54) SINGLE RECEPTOR ASSAYS FOR IMMUNOSUPPRESSIVE DRUGS

(75) Inventors: Gerald Sigler, Carmel, IN (US); Mitali Ghoshal, Fishers, IN (US); Allan Dorn, Carmel, IN (US); Shaker Rashid, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 326 days.

(21) Appl. No.: 11/468,940

(22) Filed: Aug. 31, 2006

(65) Prior Publication Data

US 2007/0054338 A1    Mar. 8, 2007

Related U.S. Application Data

(60) Provisional application No. 60/714,712, filed on Sep. 7, 2005.

(51) Int. Cl.
*G01N 33/566* (2006.01)
*G01N 33/53* (2006.01)
*C12Q 1/00* (2006.01)

(52) U.S. Cl. .............................. 435/7.1; 432/4; 432/7.8
(58) Field of Classification Search ........................ None
See application file for complete search history.

(56) References Cited

U.S. PATENT DOCUMENTS

| | | | |
|---|---|---|---|
| 5,196,352 A | 3/1993 | Siekierka et al. |
| 5,322,772 A | 6/1994 | Soldin |
| 5,354,845 A | 10/1994 | Soldin |
| 5,457,182 A | 10/1995 | Wiederrecht et al. |
| 5,498,597 A | 3/1996 | Burakoff et al. |
| 5,525,523 A | 6/1996 | Soldin |
| 5,698,448 A | 12/1997 | Soldin |
| 5,780,307 A | 7/1998 | Soldin |
| 6,410,340 B1 | 6/2002 | Soldin |

FOREIGN PATENT DOCUMENTS

WO    WO 91/04321    4/1991

OTHER PUBLICATIONS

Davis, D. et al., "An Immunophilin-Binding Assay for Sirolimus," Clinical Therapeutics, vol. 22, Supplement B, 2000, B62-71.
DeCenzo, M. et al., "FK506-binding protein mutational analysis: defining the active-site residue contributions to catalysis and the stability of ligand compleses," Protein Engineering, vol. 9, No. 2, pp. 173-180, 1996.
Galat, A. et al., "A Rapamycin-Selective 25-kDa Immunophilin," Biochemistry 1992, 31, 2427-2434.
Hung, D. et al., "cDNA Cloning of a Human 25 kDa FK506 and Rapamycin Binding Protein," Biochemical and Biophysical Research Communications, vol. 184, No. 2, 1992, 733-738.
Jin, Y. et al., "Molecular Cloning of a 25-kDa High Affinity Rapamycin Binding, FKBP25," the Journal of Biological Chemistry, vol. 267, No. 16, 10942-01945, Jun. 5, 1992 fl.
Jones, K. et al., "An Immunoassay for the Measurement of Sirolimus," Clinical Therapeutics, vol. 22, Suppl. B, 2000, B48-B61..
Liang, J. et al., "Structure of the Human 25 kDa FK506 Binding Protein Complexed with Rapamycin," J. Am. Chem. Soc. 1996, 118, 1231-1232.
Pulli, T. et al., "One-Step Homogeneous Immunoassay for Small Analytes," Anal. Chem. 2005, 77, 2637-2642.
Selvin,P., "The renaissance of fluorescence resonance energy transfer," Nature Structural biology, vol. 7, No. 9, Sep. 2000, 730-734.
Smith, D. et al., "Single-step purification of polypeptides expressed in Escherichia coli as fusions with glutathione S-transferase," Gene, 67(1988) 31-40.
Widerrecht, G. et al., "Isolation of a Human cDNA Endcoding a 25kDa Fk-506 and Rapamycin Binding Protein," Biochemical and Biophysical Research Communications, vol. 185, No. 1, 1992, 298-303.

*Primary Examiner*—Ruixiang Li
(74) *Attorney, Agent, or Firm*—Marilyn Amick; Roche Diagnostics Operations, Inc.

(57) ABSTRACT

A highly specific homogeneous assay method for an immunosuppressive drug using an immunophilin in a single receptor format is provided. In the simplest format, a single receptor is utilized analogous to a competitive immunoassay whereby an immunophilin is substituted for an antibody, and a competition results between a drug conjugate and the drug analyte for a limited number of immunophilin binding sites. In a microparticle agglutination assay format, an immunophilin is either bound to a particle or in solution. In the case where an immunophilin is bound to a particle, a polyvalent conjugate of the drug analyte is present in solution.

23 Claims, 7 Drawing Sheets

2

4

10

SINGLE RECEPTOR ASSAYS FOR IMMUNOSUPPRESSIVE DRUGS

This application claims benefit of 60/714,712 filed Sep. 07, 2005.

FIELD OF THE INVENTION

The present invention pertains to the field of therapeutic drug monitoring, and in particular, to assay for detecting and quantitating immunosuppressive drugs.

BACKGROUND OF THE INVENTION

Immunosuppressive drugs are used in immunosuppressive therapy to inhibit or prevent activity of the immune system. Clinically they are used to prevent the rejection of transplanted organs and tissues (e.g. bone marrow, heart, kidney, liver) and in the treatment of autoimmune diseases or diseases that are most likely of autoimmune origin (e.g. rheumatoid arthritis, myasthenia gravis, systemic lupus erythematosus, Crohn's disease, and ulcerative colitis).

Single receptor assays for immunosuppressive drugs such as FK506 (tacrolimus) and rapamycin (sirolimus) have used immunophilins, e.g., FKBR's (FK binding proteins), but the FKBP's show significant cross-reactivity for more than one immunosuppressive drug or for inactive metabolites. Since immunosuppressive drugs are often given in combination with each other, specificity for the parent drug is critical, and the aforementioned assays are severely limited for use in routine therapeutic drug monitoring. This problem is overcome by the use of specific FKBP's for single receptor assays. Others have tried to solve this problem by developing single receptor assays using antibodies, i.e., immunoassays, which are specific for the immunosuppressive drugs of interest. Although the immunoassays show good selectivity for the parent drugs, they generally show significant cross-reactivity to one or more inactive metabolites. This cross-reactivity tends to give an undesirable positive bias in the immunoassays when compared to chromatographic reference assays. There remains a need for specific, sensitive, and stable assays for immunosuppressive drugs, and especially for such assays which can be applied to high throughput clinical analyzers.

FKBP25 is known to be rapamycin specific, but this property has not been previously exploited for a specific assay for rapamycin. FKBP's with high cross-reactivity to both rapamycin (sirolimus) and FK506 (tacrolimus) have been used in heterogeneous single receptor assays. Single receptor assays for immunosuppressive drugs in homogeneous or heterogeneous formats which utilize antibodies are known in the art.

SUMMARY OF THE INVENTION

It is against the above background that the present invention provides certain unobvious advantages and advancements over the prior art. In particular, a need has been recognized for improvements in a single receptor assay for immunosuppressive drug substances.

Although the present invention is not limited to specific advantages or functionality, it is noted that the present invention provides a highly specific homogeneous assay method for immunosuppressive drugs using FKBP in a single receptor format. The simplest format utilizes a single receptor analogous to competitive immunoassays. Thus an immunophilin substitutes for an antibody, and a competition is set up between a drug conjugate and a drug for a limited number of immunophilin binding sites. For microparticle agglutination assays, the immunophilin is either bound to a particle or in solution. In the case where the immunophilin is bound to a particle, a polyvalent conjugate of the drug is added to the sample to be analyzed. In the case where the immunophilin is in solution, the conjugate is bound to a particle, and the immunophilin is dimerized (or polymerized) in order to bridge the particles. This is accomplished through fusion protein technology or chemical cross-linking.

For the drugs rapamycin and tacrolimus, a major challenge to the single receptor format is specificity since the class of immunophilin which binds to these drugs, the so-called FK binding proteins or FKBP's, generally do not distinguish to any significant degree between rapamycin and tacrolimus due to the structural similarities of the drugs. One exception is FKBP25, a rapamycin selective immunophilin. In a peptidyl-prolyl isomerase (rotamase) assay, a Ki of 0.9 nM for rapamycin vs. 200 nM for tacrolimus has been reported (J. Liang et al, J. Am. Chem. Soc. 118, 1231-1232, 1996).

For tacrolimus, it is possible to engineer selective FKBP12 mutants (see M. T. DeCenzo et al, Protein Engineering, 9, 173-180, 1996). Alternatively, FKBP14 has been reported to have about 20-fold lower Kd for tacrolimus (i.e., 1.8 nM) than sirolimus (40 nM) (Davis, D. et al., Clin. Therapeutics 22, Suppl. B, B62-B70, 2000), and based upon this report, FKBP14 is proposed as a candidate for an FK506 (tacrolimus) single receptor assay.

The second aspect of the invention is a sensitive homogeneous assay method for immunosuppressive drugs using FKBP's in a single receptor format. It is anticipated that increased sensitivity can be attained by use of dimeric conjugates of the immunosuppressive drug being assayed, other immunosuppressive drugs, or fragments of immunosuppressive drugs. For example, rapamycin can be dimerized through the C-40 position with a variety of linkers and used in a rapamycin single receptor assay with FKBP25 instead of aminodextran conjugates, which are typically loaded with more than two drugs. Free rapamycin is expected to compete better with these dimeric conjugates than with typical aminodextran conjugates.

The C-terminal FKBP25 peptide FKBP25C, P109-D224, (J. Liang et al.) is also useful for a rapamycin assay. J. Liang et al. reported that "The N-terminal domain does not influence the binding specificity since the C-terminal domain shows the same binding preferences as the full length protein". The N-terminal domain of FKBP25 (a~13 kDa peptide proximal to P109) may lie near the C-40 position of bound rapamycin and may hinder or reduce the binding of the aminodextran rapamycin conjugated at the C-40 position and thus reduce the sensitivity of the assay. An advantage of using FKBP25C may be improved stability since the J. Liang authors state in the supplemental material for the paper, "Recombinant hFKBP25 is unstable and degrades rapidly following purification. With time, only a mixture of fragments with molecular weights from 13.7 to 15 kDa can be identified in the original FKBP25 sample." Another potential advantage of FKBP25C may be a slight reduction in the pI as the N-terminal domain of FKBP25 is rich in basic amino acids (Galat et. al. 1992). A lower pI may reduce non-specific binding to proteins (with two pI's) in patient samples.

FKBP25 and FKBP25C are each useful in an assay for rapamycin as GST (glutathione S-transferase) fusion proteins. Fusion proteins containing the complete amino acid sequence of GST can form dimers (Amersham Biosciences, GST Gene Fusion System Handbook, page 27). GST is found in nature as a dimeric enzyme (D. B. Smith, K. S. Johnson, Gene, 67, 31, 1988). The advantage of using dimerized FKBP25 is to improve the sensitivity of an assay for rapamycin. The result of dimerization of FKBP25-GST or FKBP25C-GST fusion proteins is the formation of two binding sites per macromolecule, allowing cross-linking or binding to two identical ligands similar to an antibody. Dimerized FKBP25-GST or FKBP25C-GST fusion proteins can be used in solution to cross-link or agglutinate rapamycin coupled microparticles. Rapamycin in a sample can bind to the dimerized FKBP25-GST or FKBP25C-GST in solution and thus inhibit the agglutination of rapamycin coupled microparticles.

In accordance with one embodiment of the present invention, there is provided a method for determining the presence or amount of a target immunosuppressive drug in a sample comprising the steps of providing a sample suspected of containing the immunosuppressive drug, adding to the sample an immunophilin receptor specific for the immunosuppressive drug and a conjugate comprising the immunosuppressive drug, or an analog of the immunosuppressive drug, and a macromolecular carrier, wherein the target immunosuppressive drug and the conjugate complete for a limited number of receptor binding sites, measuring the amount of conjugate bound to the immunophilin, and correlating the amount of conjugate measured with the presence of amount of immunosuppressive drug in the sample.

In another embodiment of the present invention, there is provided a method for determining the presence or amount of a target immunosuppressive drug in a sample comprising the steps of providing a sample suspected of containing the immunosuppressive drug, adding to the sample an immunophilin receptor specific for the immunosuppressive drug and exogenous immunosuppressive drug or drug analog, wherein the immunophilin is dimerized and wherein the immunosuppressive drug and the exogenous drug or drug analog compete for a limited number of receptor binding sites, and measuring the amount of exogenous drug or drug analog bound to the immunophilin as a measure of the presence or amount of immunosuppressive drug in the sample.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings in which.

DETAILED DESCRIPTION OF THE INVENTION

Figure 1:
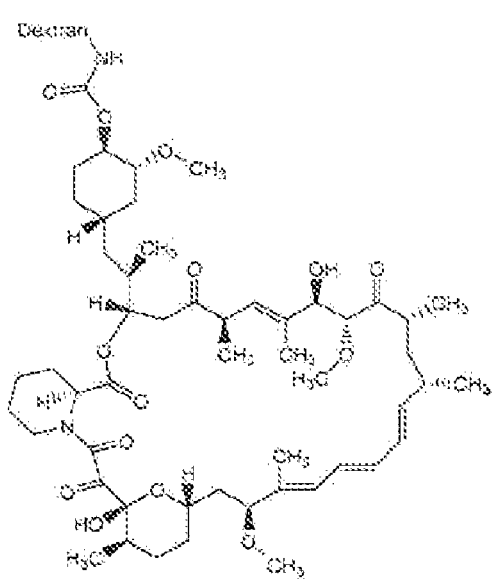
FIG. 1 illustrates representative aminodextran conjugates according to the present invention.
Figure 1:
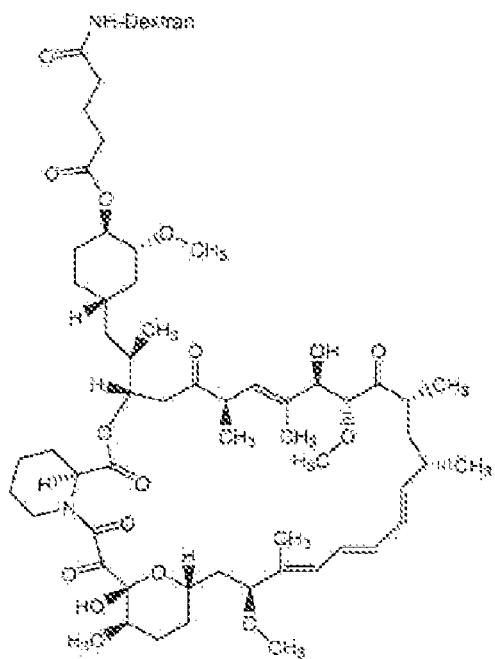
Figure 1:
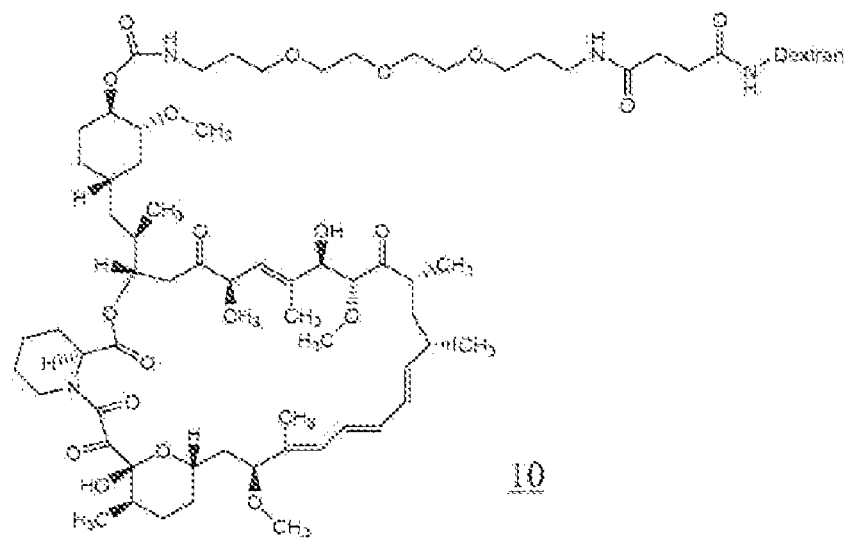

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used herein, the term "detection particle" refers to any particle having a generally spherical shape with a diameter ranging from about 10 nm to about 1000 nm that allows one to distinguish between an aggregated state and a non-aggregated state in a homogeneous assay. The size (diameter) of the detection particle can be in the nano- or a micrometer range, but for the purposes of convenience, all such particles are referred to herein as "microparticles". Detection particle includes microparticles and nanoshells. The surface of the detection particles may be functionalized, and various compounds may be attached to the surface, including for example, fluorophores, chemiluminescent entities, antibodies, biotin, or streptavidin.

An epitope is an area on the surface of an antigenic molecule that stimulates a specific immune response and against which that response is directed. Epitope tagging is a recombinant DNA method by which a protein encoded by the cloned gene is made immunoreactive to a known antibody. Development of fusion tag systems provides great flexibility for easy purification and detection of recombinant proteins using affinity matrices and specific antibodies. Epitope tags range from 10 to 15 amino acids in length and are designed to create a molecular handle for a protein. They are typically placed on either the amino or carboxyl terminus to minimize any potential disruption in tertiary structure and thus function of the protein. Because the tags are small, they are further unlikely to interfere with structure and function of the recombinant protein. Therefore, an epitope tag does not usually need to be removed before subsequent experiments are performed. A number of different tags have been used, for example, His6 (a sequence of six histidines that have a strong affinity for matrices containing metal ions like $Ni+2$ or $Co+2$), HA (a peptide sequence derived from the human influenza virus hemagglutinin protein), and AviTag, a sequence which can be enzymatically mono-biotinylated at its internal lysine residue by *E. coli* biotin protein ligase (BirA). The enzyme BirA can be added to the expression mix and the biotinylation performed in situ.

The term "specific binding" refers to a high avidity and/or high affinity binding between two paired species, including for example, such paired species as ligand/target moiety, enzyme/substrate, receptor/agonist, antibody/antigen, and lectin/carbohydrate. The binding interaction may be mediated by covalent or non-covalent interactions or a combination of covalent and non-covalent interactions. In particular, specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

The term "receptor" or "binding moiety" is used herein, refers to a protein or glycoprotein other than an antibody that specifically bind to a target compound. An example of a receptor is an immunophilin in that binds to an immunosuppressive drug.

The term "nanoshell" as used herein refers to a microparticle composed of a dielectric core (for example, silica or calcium phosphate) coated with an ultra-thin metallic layer (for example, gold). Nanoshells suitable for use in the present invention have a diameter selected from a range of about 10 nm to about 250 nm. The surface of the microparticle may be functionalized, and various compounds may be attached to the surface, including for example, antibodies or streptavidin.

The term "microparticle" as used herein refers to a solid particle of about 100 nm to about 1000 nm in diameter. Typically for use in the present invention, the microparticles will have a diameter of about 100 nm to about 600 nm. Microparticles can be formed from a variety of materials and include polystyrene and latex microparticles, the surfaces of which are optionally functionalized, and various compounds may be attached to the surface, including, for example, antibodies or streptavidin.

As used herein, the term "antibody" refers to a polypeptide or group or polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Unless otherwise stated, a general reference to an antibody encompassed polyclonal as well as monoclonal antibodies. The term "antibody" also includes recombinant proteins comprising the binding domains, as well as fragments of antibodies, including Fab, Fab', F(ab)2, and F(ab')2 fragments.

As used herein a "linker" is a bond, molecule, or group of molecules that binds two separate entities to each other. Linkers may provide for optimal spacing of the two entities or may further supply a labile linkage that allows the two entities to be separated from each other. Labile linkages include photocleavable groups, acid-labile moieties, base-labile moieties, and enzyme-cleavable groups.

As used herein, the term "homogeneous assay" refers to a quantitative or qualitative test for determining the presence or concentration of a compound in a sample, wherein the unreacted test reagents do not need to be separated from the reagents that have reacted with the target compound in order to detect, or measure the concentration of, the target compound.

As used herein the general term "immunophilin" refers to any protein receptor other than an antibody that specifically and reversibly binds to an immunosuppressive drug. For example, the term is intended to cover known protein receptors that bind to the immunosuppressive drugs cyclosporin, tacrolimus, rapamycin, and everolimus, including FK506 binding proteins (FKBP's), cyclophilin, calcineurin, and a target of rapamycin (TOR) protein, or an immunosuppressive drug binding analog of those immunophilins. Such analogs include proteins that retain a high affinity for the parent immunophilin's target immunosuppressive drug but represent a fragment of the parent protein, or a fusion protein (that includes at least a portion of the parent protein), or are derivatives of the parent immunophilin, such derivatives including one or more amino acids substitutions, deletions or insertions relative to the parent protein.

As used herein an "immunosuppressive drug analog" refers to a dimer, fragment, dimerized fragments or other derivative of the parent immunosuppressive drug that retains a high affinity for the parent drug's immunophilin.

As used herein the term "rapamycin-specific FKBP" refers to a protein that reversibly and specifically binds to rapamycin. Examples of rapamycin-specific FKBP's include FKBP25, FKBP25C, fragments of FKBP25 and FKBP25C, and fusion proteins comprising FKBP25 and rapamycin binding fragments of FKBP25.

The term "exogenous immunosuppressive drug" refers to an immunosuppressive drug that was not initially present in a sample to be analyzed for the presence of an immunosuppressive drug, but was added, typically in the form of a conjugate, during an assay. The exogenous immunosuppressive drug conjugate functions as a competitor of the immunosuppressive drug present in the sample for binding to an immunophilin.

As used herein the term "macromolecular carrier" refers to a multi-branched polymer backbone (including for example a polypeptide or carbohydrate) that can be linked to two or more compounds while allowing each of the linked compounds to specifically bind to their corresponding receptors.

As used herein the term "fluorescent energy transfer relationship" refers to a donor and acceptor fluorophore being place in sufficient proximity to one another that when the donor fluorophore is excited by incident light, the excited state energy from the donor is transferred to the acceptor fluorophore.

The present invention is directed to a homogeneous, competitive assay for detecting and determining the amount of an immunosuppressive drug (target drug) present in a sample. In accordance with one embodiment, the sample represents a biological fluid, such as blood, recovered from a patient. The assay comprises mixing the sample with a conjugate (comprising an immunosuppressive drug analog linked to a second moiety) and a receptor protein specific for the target drug. The conjugate competes with free immunosuppressive drug present in the sample for binding to the receptor protein, and detecting the amount of the conjugate bound to the receptor protein after the mixing step is used to determine the initial concentration of the immunosuppressive drug in the sample. Typically, the two assay reagents (i.e., the protein receptor and the conjugate) are added to the sample as separate components; however in one embodiment, the two reagents are added as a single composition. Either the receptor protein or the conjugate is labelled with a marker that produces a detectable signal upon binding of the receptor to the conjugate. Immunosuppressive drug present in the sample will compete with the conjugate for binding to the receptor protein, resulting in a decrease in single being generated in proportion to the concentration of the immunosuppressive drug present in the sample. Thus the method disclosed herein allows for the amount of drug present in the sample to be determined in the absence of a purification or washing step.

Labeling systems that produce a detectable signal upon the interaction of two macromolecules are known to those skilled in the art and can be adapted for use in the disclosed compositions and methods. In one embodiment, the method comprises a homogeneous particle-based assay wherein the receptor protein (e.g., an immunophilin) or the immunosuppressive drug conjugate is bound to a detection particle. Binding of the receptor protein to the conjugate species results in agglutination, whereas binding of the immunosuppressive drug present in the sample to the receptor displaces or prevents the binding of the conjugate to the receptor protein, resulting in decreased agglutination. In this embodiment, the amount of immunosuppressive drug present in the sample can be determined based on the amount of detected agglutination. More particularly, the immunosuppressive drug in the sample will compete with the immunosuppressive drug conjugate for binding to the receptor protein such that increased presence of immunosuppressive drug in the sample will result in a decreased amount of agglutination that can be detected by standard turbidity analysis.

In one embodiment, the receptor protein is labeled with a detection particle and the immunosuppressive drug conjugate comprises two or more immunosuppressive drug compounds (or two immunosuppressive drug analogs) bound together through a linker. In one embodiment, the immunosuppressive drug conjugate comprises a plurality of immunosuppressive drug compounds bound to a macromolecular carrier. In accordance with one embodiment, the macromolecular carrier is aminodextran. However any polymer structure can be used as the macromolecular carrier provided that the macromolecular carrier allows for the coupling of multiple immunosuppressive drug compounds onto the carrier in a form that allows the immunosuppressive drug to specifically bind to its corresponding immunophilin. Alternatively, the immunosuppressive drug can be formed as a dimer rather than being bound to a macromolecular carrier. For example, rapamycin can be dimerized through the C-40 position with a variety of linkers and used in a rapamycin single receptor assay instead of aminodextran conjugates. Free rapamycin is anticipated to compete better with these dimeric conjugates than with typical aminodextran conjugates.

In another embodiment, the conjugate species comprises the target immunosuppressive drug bound to a detection particle, and the receptor protein is in the form of a complex linking two or more receptor proteins to one another. In one embodiment, the receptor protein multimer is a dimer formed between two receptor proteins that are specific for the target immunosuppressive drug. In another embodiment, the receptor protein multimer comprises a plurality of receptor proteins that are linked to one another such that each linked receptor protein maintains its ability to specifically bind to the immunosuppressive drug.

In an alternative embodiment, the assay step of detecting the binding of the receptor protein and the immunosuppressive drug conjugate utilizes a fluoroscence or chemiluminescence detection system, including for example fluorescence resonance energy transfer (FRET). FRET is based upon the distance-dependent transfer of excited-state energy from a donor fluorophore to an acceptor fluorophore. The donor fluorophore is excited by incident light and if an acceptor is within 20 Å to 60 Å, the excited state energy from the donor can be transferred. Beyond the optimum range of intermolecular distances, the energy transfer efficiency falls off as the inverse sixth power of the distance. This transfer leads to a reduction in the donor's fluorescence intensity and excited-state lifetime, and an increase in the acceptor's emission intensity (Selvin, P. R. Nature Structural Biology, 2000, 7, 9, 730-734). This assay format requires that one member of a pair of FRET fluorophores be coupled to the receptor protein and one to the conjugate, respectively. A donor fluorophore such as europium and an acceptor fluorophore such as Cy5 have been used using light excitation at 340 nm and emission detection at 665 nm (Pulli, T., et. al., Analytical Chemistry, 2005, 77, 2637-2642). Several commercial kits are available to label proteins with donor and acceptor fluorophores. For example, the LANCE Eu-W 1024-ITC chelate (Perkin Elmer, AD0013) is optimized for the covalent labeling of proteins processing at least one primary aliphatic amine (N-terminus or lysine residues) with europium. Additionally, the CyDye Cy5 mono-Reactive Dye pack (Amersham, Produce Code PA23500) can be used for the covalent labeling of amine groups on proteins with Cy5. Other chemistries are available to enable labeling via amine groups (using NHS ester dyes), thiol groups (using maleimide dyes), or aldehyde groups (using hydrazide dyes).

When the receptor protein and the conjugate are labeled with one respective member of a fluorescence resonance energy transfer (FRET) fluorophore pair, binding of the receptor protein to the conjugate beings the two fluorophores within sufficient proximity to one another that upon excitation of the donor fluorophore with excitation light, fluorescent energy transfer occurs. Such an event can be measured by detecting a decrease in donor fluorophore emissions or an increase in the acceptor fluorophore's emissions. In the presence of the free drug, the fluorescence resonance energy transfer is inhibited by the competition of free drug with labeled conjugate for a limited number of binding sites on labeled receptor.

In another embodiment of the present invention, a fluorescence polarization receptor method and test kit comprises ready-to-use liquid reagents for the detection of immunosuppressive drugs using the principle of fluorescence polarization. In this assay format, an immunosuppressive drug is tagged or labeled with a fluorophore, and the corresponding immunophilin receptor is formulated in a buffer system. A competitive reaction takes place between the immunosuppressive drug with the drug-fluorophore and any free immunosuppressive drug in sample for binding to a limited amount of the corresponding specific immunophilin in the reaction solution.

When a fluorescent molecule, or fluorophore, is irradiated with light of the proper wavelength (excitation wavelength), some of the light is emitted, although at a longer wavelength (emission wavelength). Whether or not the emitted light is polarized depends on the freedom of the fluorophore to rotate in solution. A small molecule, such as fluorescein, can rotate rapidly before light emission occurs, resulting in depolarization of the emitted light. In contrast, a fluorescent macromolecule, such as a fluorescein-labeled immunosuppressive drug bound to immunophilin, will rotate much more slowly. Thus, in the time frame between excitation and emission, the macromolecule will have rotated only very slightly, and the emitted light will be polarized. Fluorescence polarization is a reproducible function of the drug concentration and is suitable for the quantitative determination of drug concentrations in samples. Thus, in this assay format, as the level of immunosuppressive drug in a sample increases, the amount of fluorescence polarization decreases.

In the present invention, the sample may be any aqueous sample that is believed to contain an immunosuppressive drug. In one embodiment, the sample is a bodily fluid isolated from a patient, including such fluids as blood, plasma, serum, urine, semen, cerebral spinal fluid, saliva and the like. In one embodiment, the sample is whole blood. In one embodiment, a blood sample is pretreated to release cellular-bound immunosuppressive drug before the sample is contacted with assay reagents. More particularly, in one embodiment, the blood sample is extracted with a solution comprising methanol and aqueous zinc sulfate, and cellular debris is removed prior to mixing the sample with the detection reagents.

When whole blood is used as the sample and the assay is based on a microparticle agglutination detection method, the blood sample is typically pretreated prior to contacting the sample with the assay reagents in order to release cellular-bound drugs. This procedure includes combining the whole blood sample with a precipitating agent. The precipitating agent is selected from those known in the art including, for example, aqueous copper sulfate or zinc sulfate in methanol, ethanol, ethylene glycol, acetonitrile or similar water miscible organic solvents. The whole blood mixture is then mixed thoroughly and centrifuged. The clear supernatant is then transferred into the sample cup and placed on the analyzer for assay performance. In one embodiment, the composition used to pretreat the whole blood sample comprises methanol and zinc sulfate. After pretreating the sample, the cellular debris is removed prior to adding the assay reagents. In one embodiment, the cellular debris is removed by centrifugation at a low speed (approximately 12,000 rpm) for 5 minutes. In one embodiment, an agglutination assay is used to detect the immunosuppressive drug wherein detection particles are nanoshells and the blood sample is not pre-treated prior to the addition of the assay reagents.

In accordance with one embodiment, a method of quantitating the amount of immunosuppressive drug present in a solution comprises mixing the sample with an immunosuppressive drug conjugate and an immunophilin specific for the target immunosuppressive drug. In one embodiment, the conjugate comprises the target immunosuppressive drug (or an immunosuppressive drug analog) bound to a macromolecular carrier and the immunophilin is bound to a detection particle, wherein the immunosuppressive drug present in the sample and the conjugate compete for binding to the immunophilin. The amount of conjugate bound to the immunophilin is then directly measured by detecting the amount of agglutination occurring the suspension. The amount of detected agglutination is then correlated to the amount of immunosuppressive drug present in the sample. In accordance with one embodiment, the macromolecular carrier is aminodextran and the detection particle is a microparticle or nanoshell.

In accordance with one embodiment, the receptor proteins are expressed as recombinant fusion proteins that include a peptide sequence that either represents a ligand or tag that is used to link a detection particle or other detection moiety to the receptor protein. In one embodiment, the fusion protein provides an optimal site for attachment of a molecule of biotin. In this embodiment, a streptavidin or avidin labeled detection particle is used to bind the detection particle to the receptor protein. For example, the receptor protein can be a recombinant protein that comprises a fusion partner with a biotinylation signal sequence. This fusion protein is co-expressed in *E. coli* or in a cell-free system with biotin ligase, e.g., AviTag, which catalyzes the covalent addition of a biotin moiety to a lysine residue in the signal sequence. In one embodiment, the receptor protein used in the assay is an AviTagged biotin labeled protein, wherein the AviTagged sequence is attached through either the C-terminus or N-terminus.

Figure 2:
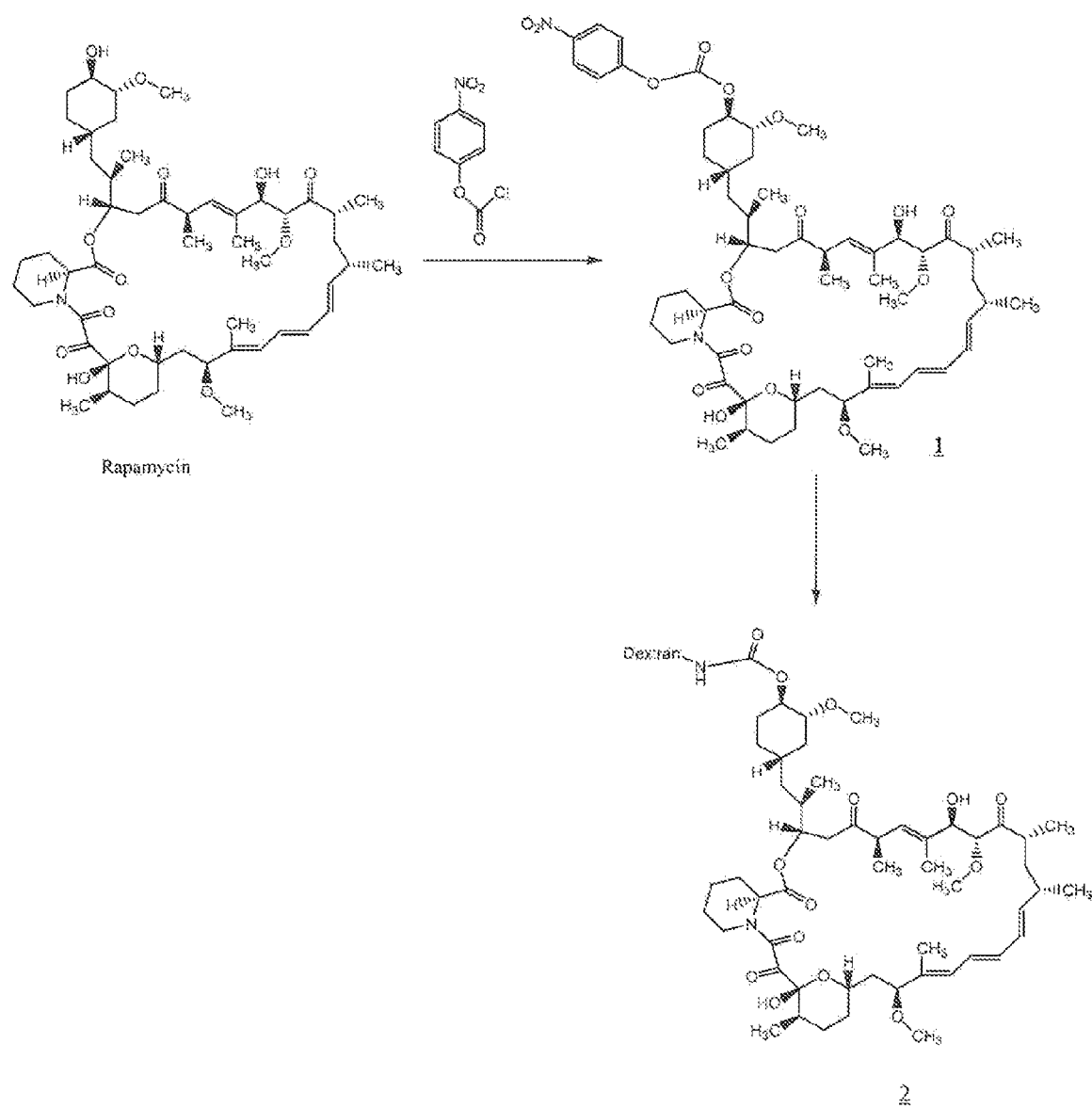
FIG. 2 illustrates the preparation of a urethane-linked rapamycin aminodextran conjugate.
Figure 3:
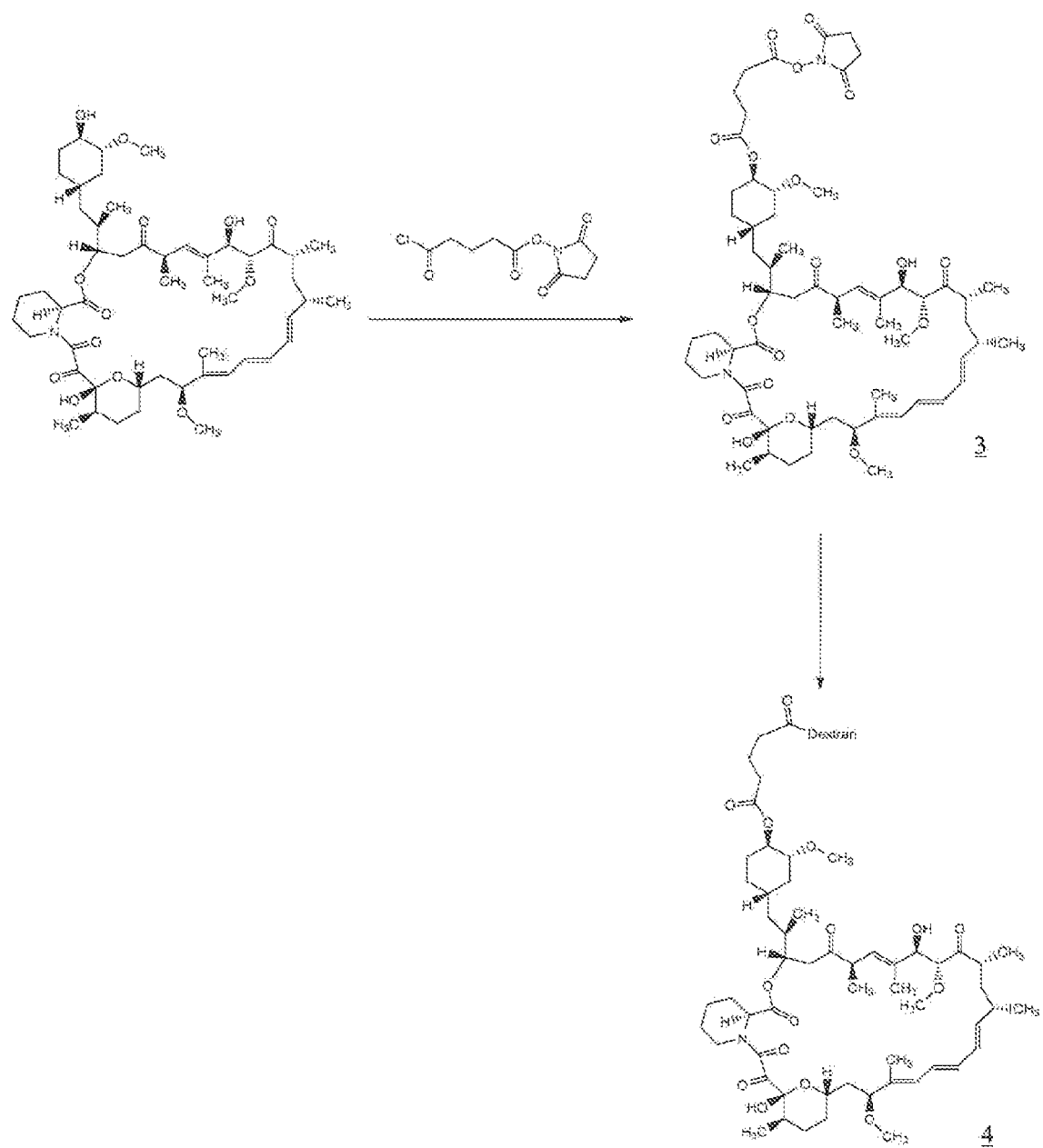
FIG. 3 illustrates the preparation of an ester-linked rapamycin aminodextran conjugate.
Figure 4:
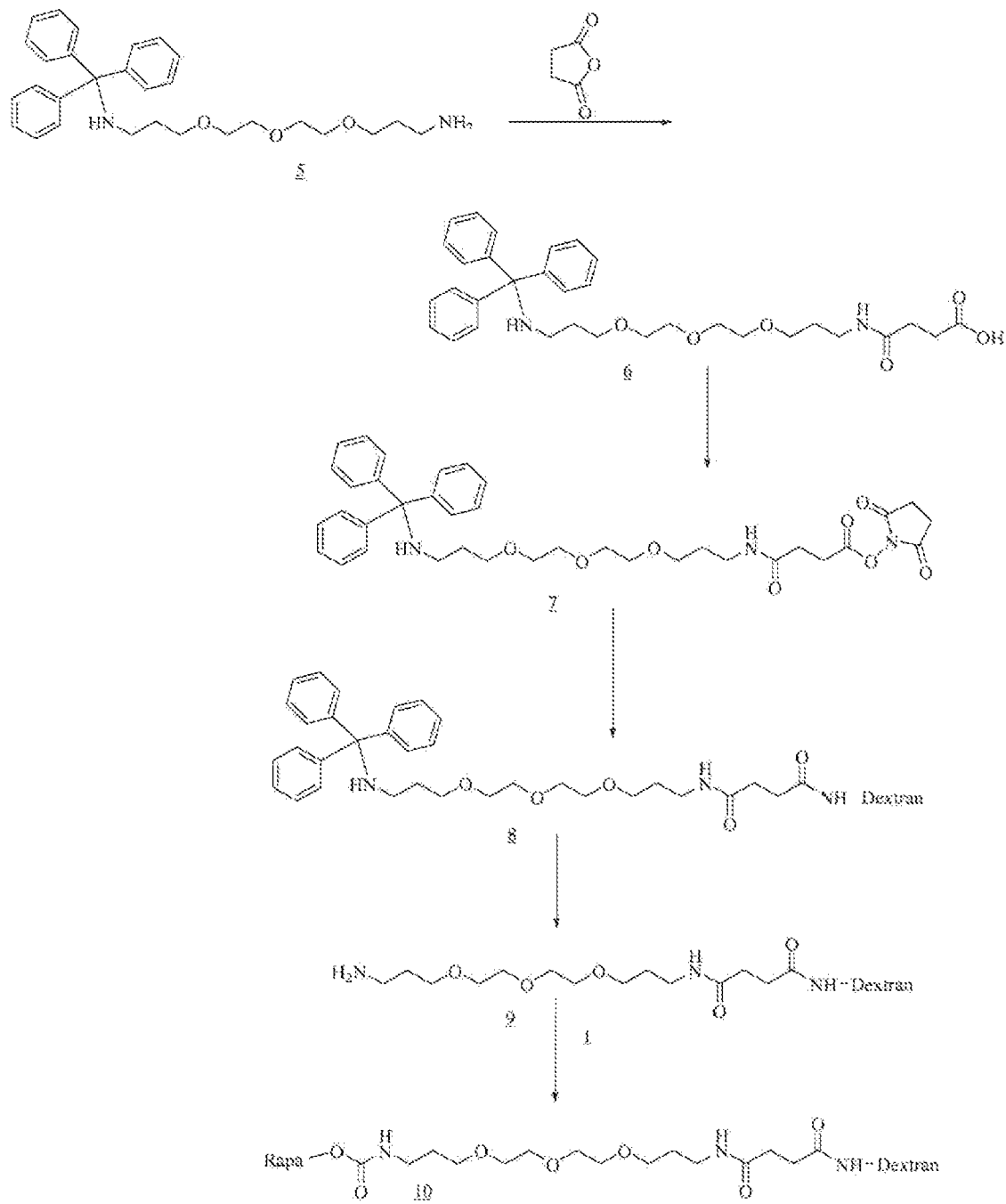
FIG. 4 illustrates the preparation of a rapamycin aminodextran conjugate with a PEG linker.
Figure 5:
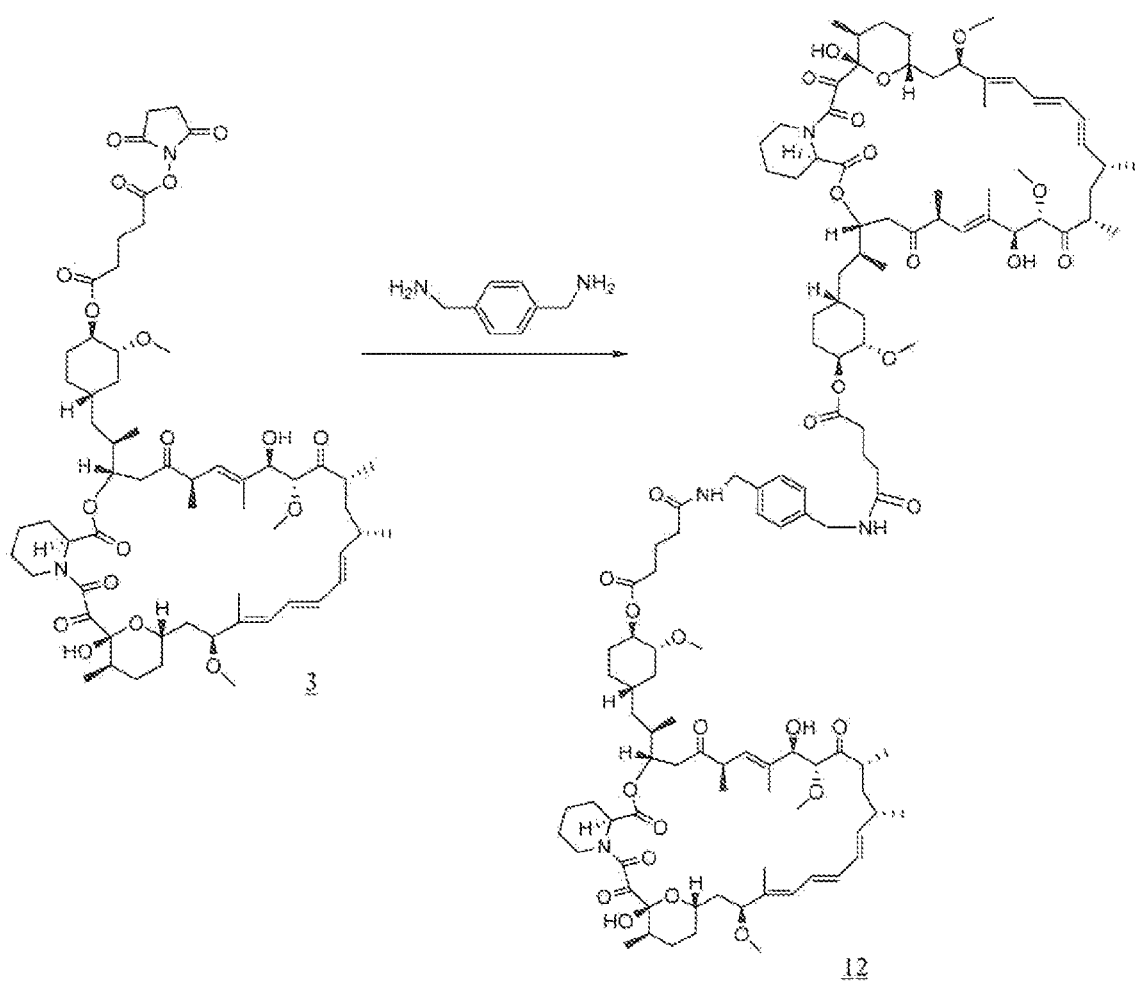
FIG. 5 illustrates the preparation of a rapamycin dimer.

The method described herein can be used to detect an immunosuppressive drug selected from the group consisting of cyclosporin, tacrolimus, rapamycin, and everolimus using receptor proteins that are specific for those drugs. In one embodiment, an agglutination assay reagent is provided for quantifying the amount of rapamycin or everolimus in a sample. In this embodiment, the protein receptor comprises a rapamycin-specific FKBP bound to a detection particle. The rapamycin-specific FKBP is conjugated to the detection particle using standard techniques including covalent binding, passing binding, or through a secondary binding interaction, such as biotin/(strept)avidin. In one embodiment, the detection particle is a microparticle, and in a further embodiment, the detection particles are bound to the immunophilin via a biotin-streptavidin or biotin-avidin linkage. Streptavidin microparticles can be either purchased or prepared by using activated microparticles and reaction with a quantity of streptavidin. In accordance with one embodiment, the rapamycin-specific FKBP is selected from the group consisting of FKBP25 and FKBP25C. A conjugate comprising rapamycin conjugated to aminodextran (AD) or an alternative macromolecular carrier, i.e. peptides, proteins, and other polysaccharides, is used as the other assay reagent. Representative aminodextran conjugates are as shown in FIG. 1. FIGS. 2, 3, and 4 describe the synthesis of aminodextran conjugates of rapamycin. The hydroxyl group of rapamycin at the C-40 position was activated using p-nitrophenyl chloroformate in pyridine. The product was coupled to aminodextran in DMSO in the presence of dimethylaminopyridine. FIG. 2 describes the synthesis of an aminodextran-rapamycin conjugate through a urethane linkage at the C-40 position. Aminodextran-rapamycin conjugates can also be made using a linker between rapamycin and aminodextran (FIG. 3). Higher sensitivity is anticipated by using a hydrophilic PEG linker to separate the immunosuppressive drug from the aminodextran molecule (FIG. 4). Alternatively, a rapamycin dimer (rapamycin-L-rapamycin where L is a linker) or other suitable multimer of rapamycin can be substituted for rapamycin-aminodextran (FIG. 5). Particle agglutination takes place in the presence of conjugate and is inhibited by free rapamycin present in the sample.

In one exemplary assay format, FKBP25 was covalently coupled to a polystyrene microparticle. Covalent attachment of FKBP25 was achieved, first by activating carboxy-modified microparticles using an activating agent, e.g. EDC/NHS (1-ethyl-3(3-dimethylaminopropyl)carbodimide/N-hydroxysuccinimide) followed by reaction with FKBP 25. The particle agglutinated in the presence of rapamycin-aminodextran conjugate, and the agglutination is inhibited in the presence of free rapamycin present in the sample to be analyzed. A rapamycin assay was achieved in the range 0-200 ng/mL (see FIG. 7).

A hydrophilic linker can also be covalently linked to the particles followed by coupling to FKBP25. This design achieves better sensitivity in the assay as well as retains better protein activity while covalently linked onto the polystyrene microparticles. Polyethylene glycol (PEG) is known in the literature to be used as a hydrophilic spacer and to reduce non-specific binding.

As noted above, attachment of protein to microparticle can also be achieved by using a streptavidin microparticle and a biotin-labeled receptor protein, FKBP 25 can be chemically monobiotinylated and used to react with a streptavidin microparticle. Monobiotinylation of FKBP25 can be achieved using the appropriate equivalence of biotin maleimide or biotin NHS ester.

Figure 6:
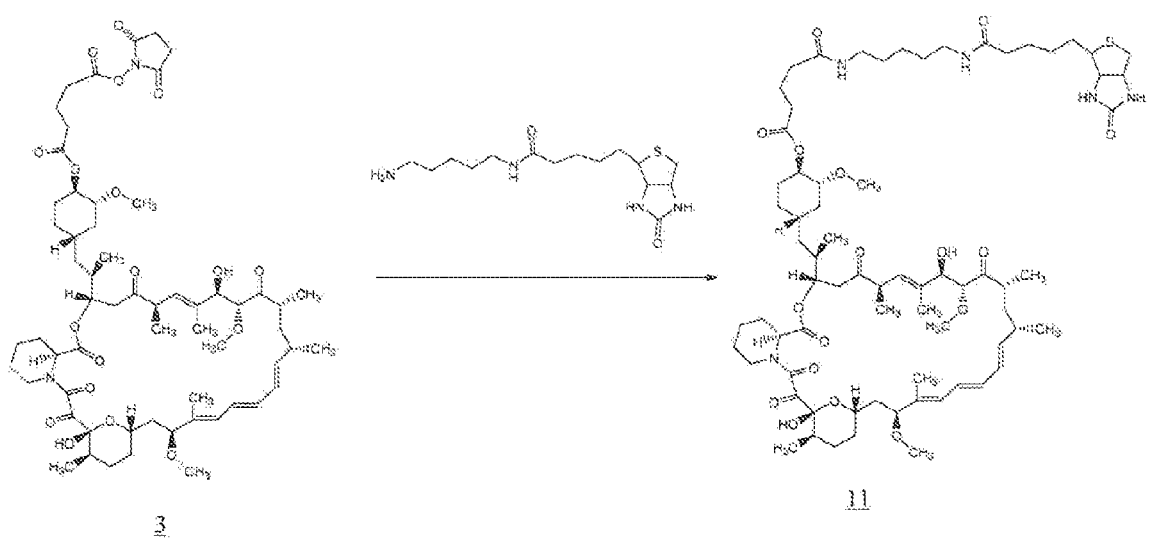
FIG. 6 illustrates the preparation of rapamycin biotin.

In another assay format, rapamycin is covalently coupled to a microparticle. This is achieved first by reaction of activated ester of rapamycin with BSA (bovine serum albumin) followed by attachment of BSA to a carboxy-modified microparticle by covalent coupling. It can also be achieved by biotinylation of rapamycin (FIG. 6) and reaction with streptavidin microparticle to provide a rapamycin-microparticle reagent.

In another embodiment, an agglutination assay reagent is provided for quantifying the amount of tacrolimus in a sample. In this embodiment, the protein receptor comprises a tacrolimus-specific FKBP bound to a detection particle. More particularly, in one embodiment, the tacrolimus-specific FKBP comprises an FKBP12 mutant that has been modified to have selectivity for tacrolimus (see M. T. DeCenzo et al, Protein Engineering 9, 173-180, 1996). In another embodiment, the tacrolimus-specific FKBP is FKBP14. The tacrolimus-specific FKBP is conjugated to a detection particle using standard techniques including covalent binding, passive binding, or through a secondary binding interaction, such as biotin/(strept)avidin. In one embodiment, the detection particle is a microparticle, and in a further embodiment, detection particles are bound to the receptor protein via a biotin-streptavidin or biotin-avidin linkage. A conjugate comprising tacrolimus conjugated to aminodextran (AD) or an alternative macromolecular carrier, i.e. peptides, proteins, and other polysaccharides, is used as the other assay reagent. Aminodextran-tacrolimus conjugates can also be made using a hydrophilic linker between tacrolimus and aminodextran.

The present invention also anticipates the generation of receptor mutants that have enhanced selectivity for the parent drug. In accordance with one embodiment, FKBP12 peptide mutants are generated using site-directed mutagenesis in order to enhance the specificity of the assay for the parent drug of rapamycin. The concept of mutating the receptor proteins in order to enhance the specificity of the receptor complex for the parent drug of rapamycin could be applied to any of the receptor proteins disclosed herein.

Accordingly, to detect the immunosuppressive drug tacrolimus, a mutant FK506 binding protein (FKBP) is used, and for the immunosuppressive drug cyclosporine, a mutant cyclophilin is used.

Publications of crystal structures can be used as an aid in the mutagenesis studies. The mutant binding proteins can be produced through recombinant methods well-known in the art and can have affinity tags added through recombinant methods to aid in their purification using methods that are also well known in the art. Accordingly, with reference to the following table, it is anticipated that the following amino acid residues can be modified to enhance the specificity of the rapamycin receptor proteins: the glutamic acid in position 54 and histidine in position 87 of FKBP12.

The following table shows C-C distances measured between rapamycin metabolites and FKBP12. The crystal structure 1fap published by the RCSB PDB (Protein Data Base) was used to measure the C-C distances of the rapamycin metabolites.

|    | PDB 1fap C—C distances | C moiety | FKBP12 (Å) |
|----|------------------------|----------|------------|
| M1 | 12-hydroxy-Rapa        | C12      | H87 (7.12) 190 (6.90) |
| M2 | 24-hydroxy-Rapa        | C24      | E54 (7.69) |
| M4 | 39-O-desmethyl-Rapa    | C52      | E54 (6.79) |

In accordance with another embodiment, a method for determining the presence or amount of an immunosuppressive drug in a sample is provided wherein the detection reagents comprise a protein receptor specific for the immunosuppressive drug and a conjugate comprising an immunosuppressive drug bound to a detection particle. In this embodiment, the protein receptor is in multimeric form, for example, a dimer of the receptor protein. The assay reagents are mixed with the sample to form a suspension wherein the conjugate and the immunosuppressive drug compete for binding to the receptor binding sites. Typically the two reagents (i.e., the protein receptor and the conjugate) are added to the sample as separate components; however, in one embodiment, the two reagents are added as a single composition. By directly measuring the amount of conjugate bound to the receptor protein in said suspension, as detected by measuring agglutination, the concentration of the target immunosuppressive drug in the sample can be determined. In one embodiment, the detection particle is a microparticle or nanoshell, and in one embodiment, the detection particle is a polystyrene latex microparticle. In a further embodiment, the sample is a blood sample obtained from a patient being administered an immunosuppressive drug, wherein the blood sample is extracted with a solution comprising methanol and aqueous zinc sulfate, and cellular debris is removed prior to mixing the sample with the assay reagents. In a further embodiment, the immunosuppressive drug to be detected is rapamycin and the immunophilin is a dimer or higher order multimer of FKBP25. In another embodiment, the immunosuppressive drug to be detected is tacrolimus and the immunophilin is a dimer or higher order multimer of a tacrolimus-specific FKBP12 mutant or FKBP14. The receptor protein dimer and multimer complexes can be formed by linking together individual receptor proteins using standard linkers known to the skilled practitioner using different linker lengths.

The present invention also encompasses a test kit containing assay reagents for measuring immunosuppressive drugs in samples. The kit may further include a variety of containers, e.g., vials, tubes, bottles, and the like. Preferably, the kit will also include instructions for use. In one embodiment, the kit comprises a protein receptor specific for the target immunosuppressive drug and a conjugate, wherein the protein receptor is bound to a detection particle, and the conjugate comprises the target immunosuppressive drug in a multimeric form. More particularly, on one embodiment, the multimeric form of the immunosuppressive drug comprises a dimer of the drug or a plurality of the drug compounds bound to a macromolecular carrier. In an alternative embodiment, the kit comprises a protein receptor specific for the target immunosuppressive drug, and a conjugate species, wherein the protein receptor is provided as a dimer or higher order multimer, and the conjugate comprises the target immunosuppressive drug bound to a detection particle. In one embodiment, a kit for detecting rapamycin is provided wherein said kit comprises a protein receptor specific for rapamycin, and a conjugate species, wherein the protein receptor is bound to a detection particle and the conjugate comprises rapamycin bound to a macromolecular carrier. More particularly, in one embodiment, the protein receptor specific for rapamycin is selected from the group consisting of FKBP25 and FKBP25C. In another embodiment, the protein receptor specific for rapamycin is FKBP25. In another embodiment, a kit for detecting tacrolimus is provided wherein said kit comprises a protein receptor specific for tacrolimus and a conjugate species, wherein the protein receptor is bound to a detection particle and the conjugate comprises tacrolimus bound to a macromolecular carrier. More particularly, in one embodiment, the protein receptor specific for tacrolimus is FKBP14.

In order that the invention may be more readily understood, reference is made to the following examples, which are intended to illustrate the invention, but not limit the scope thereof.

SPECIFIC EMBODIMENTS

EXAMPLE 1

Preparation of rapamycin 40-O-p-nitrophenyl carbonate (1)

To 100 mg (0.109 mmol) of rapamycin was added 2.5 mL of freshly distilled dichloromethane (distilled over $CaH_2$), 33 µL (0.40 mmol) of anhydrous pyridine and 33 mg (0.16 mmol) of p-nitrophenylchloroformate at −78° C. The reaction mixture was allowed to stir at −78° C. for 1 h and at room temperature for 1 h. The reaction was quenched with 50 mL of water at room temperature, and the resulting mixture was extracted with 4×50 mL of dichloromethane. The organic part was dried (anhydrous $Na_2SO_4$) and concentrated. The residue was purified by preparative HPLC using a gradient run of acetonitrile and water containing 0.1% trifluoroacetic acid. The fractions containing product were combined, concentrated in the rotary evaporator, and then lyophilized to give 82 mg (0.074 mmol, 69%) of rapamycin p-nitrophenyl carbonate (1) as a white solid. LC-MS: M+H 1101.5.

EXAMPLE 2

Preparation of 40-O-urethane Linked Rapamycin-Aminodextran Conjugate (2)

To 50 mg ($1.25 \times 10^{-3}$ mmol) of aminodextran (40,000) (prepared as in U.S. Pat. No. 6,653,456) was added 2 mL of anhydrous DMSO, and the mixture was allowed to stir for 5 minutes at room temperature. To the reaction mixture 10.7 mg (0.087 mmol) of 4-dimethylaminopyridine was added followed by a solution of 20 mg (0.018 mmol) of rapamycin p-nitrophenyl carbonate in 0.5 mL of anhydrous DMF. The reaction was allowed to stir at room temperature for 2 days. The resulting yellow solution was placed in a Spectrapor dialysis tubing (mw cut-off 2000) and dialyzed against 90% DMSO in DI water (2×3 h), 70% DMSO in DI water (1×3 hr), 50% DMSO in DI water (1×3 h), 30% DMSO in DI water (1×3 h), and 10% DMSO in DI water (1×3 h). This was followed by dialysis against DI water (6×6 h), and the resulting solution was lyophilized to give 39 mg of rapamycin-aminodextran conjugate (2) as a white solid. The incorporation of rapamycin derivative to aminodextran was measured by UV at 280 nm ($\in$=56,522) and provided 3.8 moles of rapamycin incorporation per molecule of aminodextran.

EXAMPLE 3

Perparation of Rapamycin 40-O-glutarate NHS Ester (3)

A solution of 150 mg (0.164 mmol) of rapamycin in 4 mL of dichloromethane (freshly distilled over $CaH_2$) was cooled to −78° C. To the reaction mixture was added 61 mg (0.25 mmol) of succinimido-oxycarbonyl-butyryl chloride, 15 mg (0.12 mmol) of 4-dimethylaminopyridine and 50 µL of pyridine. Succinimido-oxycarbonyl-butyryl chloride, i.e., 5-(2,5-dioxo-1-pyrrolidinyl-oxy)-5-oxo-pentanoyl chloride, was prepared according to Antonian et al., EP 0 503 454. The reaction mixture was allowed to stir at −78° C. for 2 h and LC-MS of the crude reaction mixture indicated incomplete reaction. To the reaction mixture an additional 61 mg (0.25 mmol) of succinimido oxycarbonyl butyryl chloride and 50 µL (0.60 mmol) of pyridine were added at −78° C. The resulting reaction mixture was allowed to stir at −78° C. for 2 h and then quenched with 50 mL of water. The aqueous layer was extracted with 5×50 mL of dichloromethane, and the organic layers were combined, dried (anhydrous $Na_2SO_4$), and concentrated under reduced pressure. The resulting colorless oil was dissolved in 5 mL of 4:1 acetonitrile: water and purified by preparative RP HPLC using a gradient run with a solvent system consisting of acetonitrile and water containing 0.1% trifluoroacetic acid. Fractions containing the product were combined, concentrated in the rotary evaporator and lyophilized to give 70 mg (0.062 mmol, 38%) of rapamycin NHS ester (3) as a white solid, LR-ES; M+Na 1147.2.

EXAMPLE 4

Preparation of 40-O-glutaryl Rapamycin Aminodextran Conjugate (4)

To 50 mg ($2.5 \times 10^{-5}$ mmol) of aminodextran (40,000) and 7.5 mg (0.062 mmol) of 4-dimethylaminopyridine was added 2 mL of anhydrous DMSO (dimethyl sulfoxide) and allowed to stir at room temperature for 15 minutes. To the reaction mixture a solution of 20 mg (0.017 mmol) of rapamycin 40-O-glutarate NHS ester (3) in 1 mL of anhydrous DMF was added dropwise and the reaction mixture was allowed to stir at room temperature for 2 days. The resulting reaction mixture was placed in a Spectrapor dialysis tubing (mw cut off 2000) and dialyzed against 90% DMSO in DI water (2×3 h), 70% DMSO in DI water (1×3 h), 50% DMSO in DI water (1×3 h), 30% DMSO in DI water (1×3 h), and 10% DMSO in DI water (1×3 h). This was followed by dialysis against DI water (6×6 h) and the resulting solution was lyophilized to give 49 mg of aminodextran conjugate (4) as a white solid. The incorporation of rapamycin derivative to aminodextran was measured by UV at 280 nm ($\in$=56.522) and provided 5.4 moles of rapamycin incorporated per molecule of aminodextran.

EXAMPLE 5

Preparation of N-succinyl-NH-$(PEG)_2$-NH-trityl (6)

To a solution of 100 mg (0.21 mmol) of N-trityl-4,7,10-trioxa-1,13-tridecane-diamine [Trt-NH-$(PEG)_2$-$NH_2$, NOVA Biochem] (5) in 3 mL of freshly distilled dichloromethane was added 35 µL (0.42 mmol) of pyridine, 13.2 mg (0.108 mmol) of 4-dimethylaminopyridine and 32.4 mg (0.32 mmol) of succinic anhydride. The reaction mixture was allowed to stir at room temperature 18 h and concentrated. The residue was purified by preparative RP HPLC using a gradient consisting of acetonitrile and water. Fractions containing the desired product were combined and lyophilized to give 119 mg (0.21 mmol, 99%) of N-succinyl-NH-$(PEG)_2$-NH-trityl (6) as colorless oil. LC-MS: M+H 563.3.

EXAMPLE 6

Preparation of trityl-NH-$(PEG)_2$-N-succinyl-N-hydroxysuccinimide ester (7)

To 115 mg (0.20 mmol) of N-succinyl-NH-$(PEG)_2$-NH-trityl (6) was added 5 mL freshly distilled THF and 114 µL (0.64 mmol) of N,N-diisopropylethyl amine and 192 mg (0.63 mmol) of O—(N-succinimidyl)-N,N,N',N'-tetramethyluronium tetrafluoroborate. The reaction mixture was allowed to stir at room temperature for 3 h and concentrated. To the residue 15 mL of water was added and the aqueous reaction mixture was extracted with 2×15 mL of dichloromethane. The organic layers were combined and washed with 2×15 mL of saturated $NaHCO_3$ solution followed by 1×15 mL of water. The organic layer was dried (anhydrous $Na_2SO4$) and concentrated to give 90 mg (0.136 mmol, 67%) of trityl-NH-$(PEG)_2$-N-succinyl-N-hydroxysuccinimide ester (7) as colorless oil. This was used in the next step immediately without further purification. LC-MS: M+H 660.3.

EXAMPLE 7

Preparation of trityl-NH-$(PEG)_2$-N-succinyl-aminodextran conjugate (8)

To 200 mg ($5 \times 10^{-3}$ mmol) of aminodextran (40,000) was added 10 mL of DMSO and allowed to stir at room temperature to dissolve and 280 µL (1.9 mmol) of triethylamine was added. To the reaction mixture a solution of 90 mg (0.136 mmol) of trityl-NH $(PEG)_2$-N-succinyl-N-hydroxysuccinimide ester (7) in 5 mL of anhydrous DMSO was added and the resulting reaction mixture was allowed to stir at room temperature for 3 days. The resulting reaction mixture was placed in a Spectrapor dialysis tubing (mw cut off 2000) and dialyzed against 90% DMSO in DI water (2×3 h), 70% DMSO in DI water (1×3 h), 50% DMSO in DI water (1×3 h), 30% DMSO in DI water (1×3 h), and 10% DMSO in DI water (1×3 h). This was followed by dialysis against DI water (6×6 h) and the resulting solution was lyophilized to give 180 mg of white solid. The incorporation of Trityl PEG derivative to aminodextran was measured by UV at 230 nm ($\in$=2727) and provided 9.6 moles of Trit-PEG incorporation per molecule of aminodextran.

EXAMPLE 8

Preparation of amino-(PEG)$_2$-N-succinyl-aminodextran conjugate (9)

To 180 mg of trityl-NH-(PEG)$_2$-N-succinyl-aminodextran conjugate (8) was added 10 mL of dichloromethane and allowed to stir at room temperature for 15 minutes. To the reaction mixture was added 10 mL of trifluoroacetic acid and allowed to stir at room temperature for 45 minutes. The reaction mixture was concentrated; 10 mL of dichloromethane was added and concentrated under reduced pressure. The process of addition of dichloromethane and concentration was repeated two more times. To the residue 10 mL of water was added and the resulting reaction mixture was placed in a Spectrapor dialysis tubing (mw cut off 2000) and dialyzed against 90% DMSO in DI water (2×3 h), 70% DMSO in DI water (1×3 h), 50% DMSO in DI water (1×3 h), 30% DMSO in DI water (1×3 h), 10% DMSO in DI water (1×3 h). This was followed by dialysis against DI water (6×6 h) and the resulting solution was lyophilized to give 140 mg of amino-(PEG)$_2$-N-succinyl-aminodextran conjugate trifluoroacetate salt (9) as a white solid.

EXAMPLE 9

Preparation of Rapamycin-(PEG)$_2$-N-succinyl-aminodextran Conjugate (10)

To 50 mg (1.25×10$^{-3}$ mmol) of amino-(PEG)$_2$-N-succinyl-aminodextran conjugate trifluoroacetate salt (9) was added 2 mL of anhydrous DMSO and allowed to stir for 5 minutes to dissolve. To the reaction mixture was added a solution of 20 mg (0.018 mmol) of rapamycin p-nitrophenyl carbonate (1) in 1 mL of anhydrous DMF containing 7.6 mg (0.062 mmol) of 4-dimethylaminopyridine and allowed to stir at room temperature for 2 days. The resulting reaction mixture was placed in a Spectrapor dialysis tubing (mw cut off 2000) and dialyzed against 90% DMSO in DI water (2×3 h), 70% DMSO in DI water (1×3 h), 50 % DMSO in DI water (1×3 h), 30% DMSO in DI water (1×3 h), and 10% DMSO in DI water (1×3 h). This was followed by dialysis against DI water (6×6 h) and the resulting solution was lyophilized to give 52 mg of rapamycin-(PEG)$_2$-N-succinyl-aminodextran conjugate (10) as a white solid. The incorporation of rapamycin derivative to aminodextran was measured by UV at 280 nm ($\in$=56.522) and provided 2.9 moles of rapamycin incorporation per molecule of aminodextran.

EXAMPLE 10

Preparation of Rapamycin Biotin Conjugate (11)

To a solution of 59 mg (0.052 mmol) of rapamycin 40-O-glutarate NHS ester (3) in 2.5 mL of anhydrous N,N-dimethylformamide was added 30 mg (0.09 mmol) of EZ-Link 5-(biotinamide) pentylamine (Pierce) followed by 10 mg (0.081 mmol) of 4-dimethylaminopyridine and 23 µL (0.27 mmol) of anhydrous pyridine. The resulting reaction mixture was allowed to stir at room temperature for 2 h and concentrated. The residue was purified by preparative RP HPLC using a gradient consisting of acetonitrile and water containing 0.1% trifluoroacetic acid. Fractions containing the desired product were concentrated and lyophilized to give 23 mg (0.017 mmol, 33%) of rapamycin biotin conjugate (11) as a white solid. LC-MS: M+Na 1361.7.

EXAMPLE 11

Preparation of Rapamycin Dimer (12)

A stock solution of 2.0 mg of p-xylylenediamine in 6 mL of freshly distilled THF was prepared. The mixture was allowed to stir for 10 minutes at room temperature and then 20 mg of 4-dimethylaminopyridine was added. In another flask a solution of 30 mg (0.026 mmol) of rapamycin 40-O-glutarate NHS ester (3) in 5 mL of freshly distilled THF was prepared. To the reaction mixture 2.5 mL of the p-xylylenediamine (6.1×10$^{-3}$ mmol)/4-dimethylaminopyridine (0.068 mmol) stock solution was added at 4° C. and the reaction mixture was allowed to stir at 4° C. for 18 h. The reaction mixture was concentrated under reduced pressure and purified by preparative thin layer chromatography using ethyl acetate as eluent to give 20 mg (9.27×10$^{-3}$ mmol, 35%) of rapamycin dimer (12) as a white solid. HR-MS (+) Calculated for $C_{120}H_{178}N_4O_{30}$ [M+2Na]$^2$ 1100.6155; observed 1100.6151.

EXAMPLE 12

Preparation of FKBP25 Microparticle

To 5 ml of 10% carboxylated modified polystyrene microparticles (0.302 mm) with 0.216 mEq/g of carboxyl content (Seradyn, Indianapolis) was added 45 mL of DI water. This was centrifuged at 14,000 rpm at 4 degrees C. for 45 minutes and the supernatant was decanted. This was resuspended in 50 mM MES buffer (pH 6.3) and centrifuged. This process was repeated twice and the concentration of the microparticle was adjusted to 1% (w/v). The concentration measurement was performed by COBAS MIRA analyzer (Roche Diagnostics, Indianapolis).

To a suspension of 45 mL of 1% carboxylated microparticle preparation was added a solution of 939 mg of EDC and 563 mg of N-hydroxysuccinimide in 45 mL of 50 mM MES buffer (pH 6.3) at room temperature. The reaction mixture was allowed to stir 18 h at room temperature. The reaction mixture was poured into centrifuge tube and centrifuged at 14,000 rpm at 4 degree C. for 45 minutes, the solids were resuspended in 50 mM MOPS (pH 7.9) buffer and centrifuged as above. This process was repeated twice and the activated microparticle preparation was adjusted to a concentration of 1% (w/v) in 50 mM MOPS (pH 7.9).

To 8 ml of 1% activated microparticle preparation in 50 mM MOPS buffer (pH 7.9) was added a solution of 1 mg of FKBP25 in 4 mL of 50 mM MOPS buffer all at once at room temperature. The reaction mixture was allowed to stir at room temperature for 2 h and the reaction mixture was quenched with 5 mL of 1M aqueous ethanolamine (pH 9). The reaction was allowed to stir at room temperature 18 h. This was transferred to centrifuge tube and centrifuged at 14,000 rpm at 4 degree C. for 45 minutes, the solids were resuspended in 50 mM MOPS (pH 7.9) buffer and centrifuged as above. This process was repeated twice and the activated microparticle preparation was adjusted to a concentration of 0.14% (w/v) in 50 mM MOPS (pH 7.9). A total of 38 mL at 0.14% (w/v) of FKBP25 microparticle preparation was obtained. This FKBP 25 microparticle preparation was used as R2 reagent in the development of rapamycin assay as described in Example 14 below.

EXAMPLE 13

Preparation of PEG-Modified FKBP25 Microparticle

To 10 ml of 1% (w/v) activated microparticle (prepared as described in Example 12) in 50 mM MOPS buffer (pH 7.9) was added 10 mL solution of 21 mg (0.047 mmol) of dPEG8 (Quanta Biodesign) in 50 mM potassium phosphate at pH 9. The reaction mixture was allowed to stir at room temperature for 18 h. This was transferred to centrifuge tubes and centrifuged at 14,000 rpm at 4 degree C. for 45 minutes, the solids were resuspended in 50 mM MES (pH 6.3) buffer and centrifuged as above. This process was repeated twice and PEG-modified microparticle preparation was adjusted to a concentration of 0.9% in 50 mM MES buffer (pH 6.3). A total of 10 mL of 0.9% (w/v) PEG-microparticle preparation was obtained To all of the above was added 10 mL of a solution of 187 mg of EDC and 112 mg of NHS in 50 nM MES buffer (pH 6.3). The reaction mixture was allowed to stir at room temperature 18 h. The reaction mixture was poured into centrifuge tubes and centrifuged at 14,000 rpm at 4 degree C. for 45 minutes, the solids were resuspended in 50 mM MOPS (pH 7.9) buffer and centrifuged as above. This process was repeated twice and the activated microparticle was adjusted to a concentration of 0.88% (w/v) in 50 mM MOPS (pH 7.9). A total of 10 mL at 0.88% (w/v) concentration in 50 mM MPOS buffer (pH 7.9) of activated PEG linked microparticle preparation was obtained.

To 4 mL of 0.88% (w/v) of activated PEG-microparticle was added a solution of 424 µg of FKBP25 in 2 mL of 50 mM MOPS (pH 7.9). The reaction mixture was allowed to stir at room temperature for 2 h and the reaction was quenched with 5 mL of 1M ethanolamine (pH 9). This was transferred to a centrifuge tube and centrifuged at 14,000 rpm at 4 degree C. for 45 minutes, the solids were resuspended in 50 mM MOPS (pH 7.9) buffer and centrifuged as above. This process was repeated twice and the activated microparticle was adjusted to a concentration of 0.14% (w/v) in 50 mM MOPS (pH 7.9). A total of 16 mL at 0.14% (w/v) of FKBP25-PEG microparticle preparation was obtained. This FKBP 25-PEG microparticle preparation was used as R2 reagent in the development of rapamycin assay.

EXAMPLE 14

Dose-Response Curve for FKBP25 Microparticles and Rapamycin-Aminodextran (Assay for Rapamycin)

A first working reagent (R1 reagent) was prepared by making 175 mM PIPES buffer, pH 7.4. To this was added rapamycin-aminodextran conjugate to give a concentration of 400 ng/mL. To this was also added polyacrylic acid to give a concentration of 1.3%.

A second working reagent (R2 reagent) was prepared as described in Example 12 and used at final concentration of 0.14% (w/v) in 50 mM MOPS buffer at pH 7.9.

A stock solution of rapamycin was made (100 µg/mL) in DMSO. Calibrators were prepared from the stock by making solution of 50, 100 and 200 ng/mL of rapamycin in 0.9% saline solution.

Figure 7:
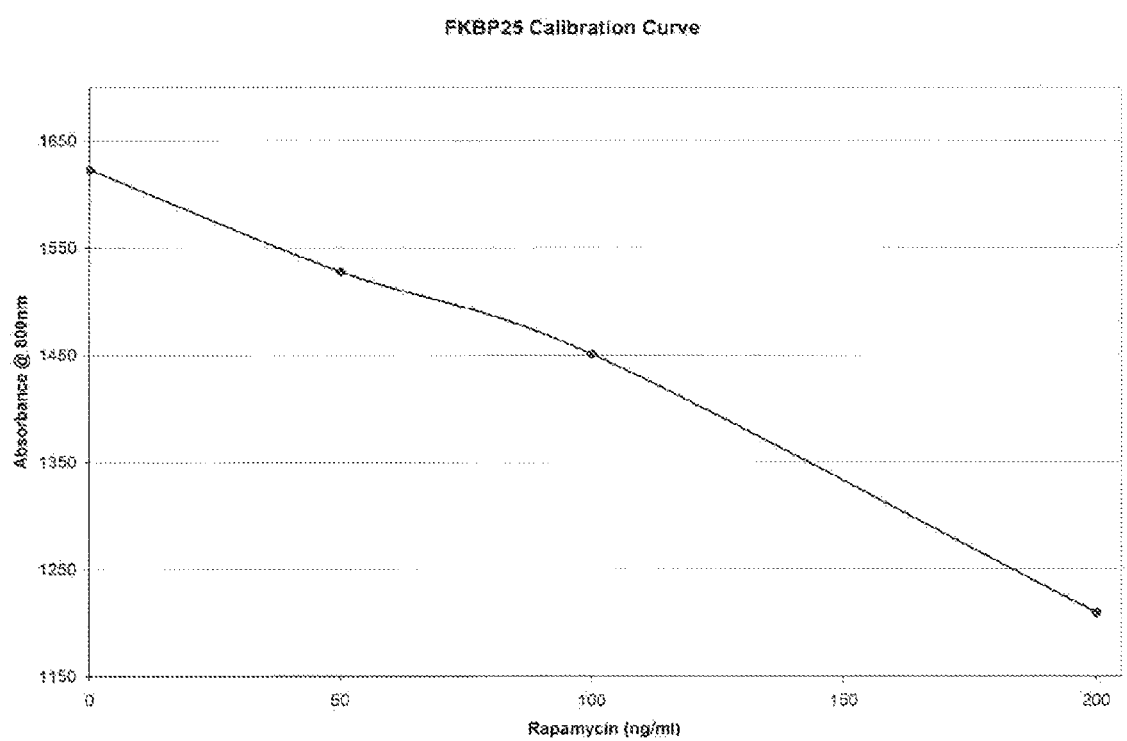
FIG. 7 shows the dose-response curve described in Example 14.

An assay was performed using a Hitachi 917 automated analyzer (Roche Diagnostics Corporation, Indianapolis) using a 35 µL sample volume, 180 µL of the first working reagent and 80 µL of the second working reagent (measured OD at 800 nm). Results are shown in FIG. 7.

Known quantities of tacrolimus were then assayed as above. By comparing the observed reading from the rapamycin curve obtained to the actual amount of tacrolimus in the samples assayed, tacrolimus cross-reactivity was determined to be 7% in this assay. That is, a sample containing 1000 ng/ml tacrolimus gave a reading from the curve of 70 ng/ml rapamycin. Cross-reactivity is thus (70/1000)×100%=7%.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for determining the presence or amount of an immunosuppressive drug in a sample comprising the steps of:
providing a sample suspected of containing the immunosuppressive drug,
mixing the sample with a conjugate and an immunophilin receptor specific for the immunosuppressive drug to form a suspension, wherein the immunophilin receptor is bound to detection particles and the conjugate comprises an exogenous immunosuppressive drug or drug analog bound to a macromolecular carrier, wherein the immunosuppressive drug present in the sample and the exogenous drug or drug analog compete for binding to the immunophilin receptor, and the detection particles agglutinate upon binding of the immunophilin receptor with the exogenous drug or drug analog,
measuring the amount of particle agglutination in the suspension, and
correlating the amount of agglutination measured with the presence or amount of immunosuppressive drug in the sample, wherein the immunosuppressive drug is selected from the group consisting of tacrolimus and rapamycin.

2. The method of claim 1 wherein the sample is a blood sample obtained from a patient being administered an immunosuppressive drug.

3. The method of claim 1 wherein the blood sample is extracted with a solution comprising methanol and zinc sulfate, and cellular debris is removed prior to the mixing step.

4. The method of claim 1 wherein the macromolecular carrier is selected from the group consisting of peptides, proteins, and polysaccharides.

5. The method of claim 1 wherein the macromolecular carrier is aminodextran.

6. The method of claim 1 wherein the immunosuppressive drug is rapamycin and the immunophilin receptor is a rapamycin-specific FK binding protein.

7. The method of claim 1 wherein the immunosuppressive drug is rapamycin and the immunophilin receptor is a rapamycin-specific EK binding protein selected from the group consisting of FKBP25 and FKBP25C.

8. The method of claim 1 wherein the immunosuppressive drug is tacrolimus and the immunophilin receptor is a tacrolimus-specific FK binding protein.

9. The method of claim 1 wherein the immunosuppressive drug is tacrolimus and the immunophilin receptor is a tacrolimus-specific FK binding protein selected from the group consisting of a tacrolimus-specific FKBP12 mutant or FKBP14.

10. The method of claim 1 wherein the detection particles are microparticles or nanoshells.

11. The method of claim 1 wherein the detection particles are bound to the immunophilin receptor via a biotin-streptavidin or biotin-avidin linkage.

12. A method for determining the presence or amount of an immunosuppressive drug in a sample comprising the steps of:
   providing a sample suspected of containing the immunosuppressive drug,
   mixing the sample with a conjugate and an immunophilin receptor specific for the immunosuppressive drug to form a suspension, wherein the conjugate comprises an exogenous immunosuppressive drug or drug analog bound to detection particles, and the immunophilin receptor is in multimeric form, wherein the immunosuppressive drug and the exogenous immunosuppressive drug or drug analog compete for binding to the immunophilin receptor, and the detection particles agglutinate upon binding of the immunophilin receptor with the exogenous drug or drug analog,
   measuring the amount of particle agglutination in the suspension, and
   correlating the amount of agglutination measured with the presence or amount of immunosuppressive drug in the sample, wherein the immunosuppressive drug is selected from the group consisting of tacrolimus and rapamycin.

13. The method of claim 12 wherein the sample is a blood sample obtained from a patient being administered an immunosuppressive drug.

14. The method of claim 12 wherein the blood sample is extracted with a solution comprising methanol and zinc sulfate, and cellular debris is removed prior to the mixing step.

15. The method of claim 12 wherein the immunophilin receptor is in dimeric form.

16. The method of claim 12 wherein the immunosuppressive drug is rapamycin and the immunophilin receptor is a rapamycin-specific FK binding protein.

17. The method of claim 12 wherein the immunosuppressive drug is rapamycin and the immunophilin receptor is a rapamycin-specific FK binding protein selected from the group consisting of FKBP25 and FKBP25C.

18. The method of claim 12 wherein the immunosuppressive drug is tacrolimus and the immunophilin receptor is a tacrolimus-specific FK binding protein.

19. The method of claim 12 wherein the immunosuppressive drug is tacrolimus and the immunophilin receptor is a tacrolimus-specific FK binding protein selected from the group consisting of a tacrolimus-specific FKBP12 mutant or FKBP 14.

20. The method of claim 12 wherein the detection particles are microparticles or nanoshells.

21. The method of claim 12 wherein the detection particles are microparticles bound to the receptor protein via a biotin-streptavidin or biotin-avidin linkage.

22. A method for determining the presence or amount of rapamycin in a sample comprising the steps of:
   providing a sample suspected of containing rapamycin,
   mixing the sample with a rapamycin dimer and an immunophilin receptor specific for rapamycin to form a suspension, wherein the immunophilin receptor is bound to detection particles, wherein the rapamycin in the sample and the rapamycin dimer compete for binding to the immunophilin receptor, and the detection particles agglutinate upon binding of the immunophilin receptor with the rapamycin dimer,
   measuring the amount of particle agglutination in the suspension, and
   correlating the amount of agglutination measured with the presence or amount of rapamycin in the sample.

23. The method of claim 22 wherein the immunophilin receptor is a rapamycin-specific FK binding protein selected from the group consisting of FKBP25 and FKBP25C.

* * * * *

UNITED STATES PATENT AND TRADEMARK OFFICE
CERTIFICATE OF CORRECTION

PATENT NO.       : 7,642,059 B2                                    Page 1 of 1
APPLICATION NO.  : 11/468940
DATED            : January 5, 2010
INVENTOR(S)      : Sigler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 453 days.

Signed and Sealed this

Sixteenth Day of November, 2010

David J. Kappos
*Director of the United States Patent and Trademark Office*